(12) United States Patent
Dai et al.

(10) Patent No.: US 9,610,022 B1
(45) Date of Patent: Apr. 4, 2017

(54) ADAPTIVE OPTICAL OBJECTIVE INSPECTION INSTRUMENT FOR OPTIC NERVE FUNCTION

(71) Applicant: THE INSTITUTE OF OPTICS AND ELECTRONICS, THE CHINESE ACADEMY OF SCIENCES, Chengdu, Sichuan (CN)

(72) Inventors: Yun Dai, Chengdu (CN); Haoxin Zhao, Chengdu (CN); Yudong Zhang, Chengdu (CN)

(73) Assignee: The Institute of Optics and Electronics, The Chinese Academy of Sciences, Sichuan (CN)

( * ) Notice: Subject to any disclaimer, the term of this patent is extended or adjusted under 35 U.S.C. 154(b) by 0 days.

(21) Appl. No.: 14/971,032

(22) Filed: Dec. 16, 2015

(30) Foreign Application Priority Data

Oct. 19, 2015 (CN) .......................... 2015 1 0679438

(51) Int. Cl.
| | |
|---|---|
| *A61B 3/10* | (2006.01) |
| *A61B 5/04* | (2006.01) |
| *A61B 3/00* | (2006.01) |
| *A61B 3/14* | (2006.01) |
| *G02B 27/00* | (2006.01) |

(52) U.S. Cl.
CPC ........ *A61B 5/04001* (2013.01); *A61B 3/0025* (2013.01); *A61B 3/0041* (2013.01); *A61B 3/1015* (2013.01); *A61B 3/14* (2013.01); *G02B 27/0068* (2013.01)

(58) Field of Classification Search
USPC ....................................................... 351/221
See application file for complete search history.

(56) References Cited

U.S. PATENT DOCUMENTS

2012/0154746 A1    6/2012   Nozato

FOREIGN PATENT DOCUMENTS

| CN | 2565080 Y | 8/2003 |
|---|---|---|
| CN | 1601231 A | 3/2005 |
| CN | 101926640 A | 12/2010 |

(Continued)

OTHER PUBLICATIONS

First Office Action of the corresponding Chinese Patent, Application No. 201510679438.1 mailed on May 4, 2016, 5 pages.

*Primary Examiner* — Jack Dinh
(74) *Attorney, Agent, or Firm* — Knobbe, Martens, Olson & Bear LLP

(57) ABSTRACT

An adaptive optical objective inspection instrument for optic nerve function comprises: a sub-system for measuring wave aberration of human's eyes, including a near infrared beacon light source, an intermediate optical system, a wavefront corrector and a wavefront sensor, configured to measure and obtain wave aberration of testee's eyes, the intermediate optical system arranged along an optical path between the near infrared beacon light source and the wavefront sensor, and the wavefront corrector arranged in the optical path of the intermediate optical system; a sub-system for correcting wave aberration of human's eyes, including the intermediate optical system, the wavefront corrector and a control unit, the control unit configured to drive and control the wavefront corrector to correct the wave aberration of testee's eyes according to the measured wave aberration; and a sub-system for inspecting optic nerve function, including a visual stimulus display and a system for collecting visual evoked potential signal.

9 Claims, 2 Drawing Sheets

(56) References Cited

FOREIGN PATENT DOCUMENTS

| | | |
|---|---|---|
| CN | 101947158 A | 1/2011 |
| CN | 102028449 A | 4/2011 |
| CN | 102551657 A | 7/2012 |
| CN | 103211575 A | 7/2013 |
| CN | 104127169 A | 11/2014 |
| EP | 2322080 A1 | 5/2011 |
| JP | 2005-224328 A | 8/2005 |
| JP | 2011-104135 A | 6/2011 |

ADAPTIVE OPTICAL OBJECTIVE INSPECTION INSTRUMENT FOR OPTIC NERVE FUNCTION

TECHNICAL FIELD

The present disclosure relates to an adaptive optical objective inspection instrument for optic nerve function by measuring and correcting aberration of human's eyes through an adaptive optical system as well as visually stimulating a retina by flashing or an image in such a situation.

BACKGROUND

A visual evoked potential (VEP) is also called as a visual evoked reaction, which is an electrical reaction of an visual center of an occipital lobe recorded in the dermal surface of the head when the retina is stimulated by flashing or an image and then the signal is delivered along an optic pathway. It mainly reflects a transfer function from a ganglion cell of the retina to the visual cortex. The $17^{th}$ region of the visual cortex in the cerebral cortex mainly receives projection of nerve fibers within 10 degree in the central retina 100, and the projection region is nearest to the scalp surface, so most of information about the VEP is originated from macula lutea region. The VEP not only reflects a function of a visual cortex of the occipital lobe, but also reflect a function of a transfer channel from the macula lutea region of the retina and a ganglion cell of the macula lutea region to the visual cortex. VEP is an important method for objectively evaluating and inspecting the visual nerve function (cf. Yingfu PAN, Clinical evoked potential, Edition 2, People's medical publishing house).

The Visual evoked potential is an electrical reaction of the occipital lobe of the cerebral cortex on the visual stimulation and represents a potential change caused by the stimulation received by the retina and conducted to the cortex of the occipital lobe through the visual pathway. As can be seen from a mechanism for generating the visual evoked potential, no matter which of the visual evoked potential, it is the most import that the retina receives visual stimulation and the stimulation on the retina has to be projected through the dioptric system of the human's eyes. Thus, the quality of an optical system of the human's eyes will directly affect the quality of the stimulation projected onto the retina. For the transfer of the visual stimulation to the retina, except for diffraction generated by the pupil of the human's eyes which is incapable of being avoiding, the optical aberration is the most important influential factor. It is well known for the people that the optical system of the human's eyes is not an ideal optical system. Except for the low-order aberrations such as defocus and astigmatism, there are many high order aberrations having more complex shape (e.g. spherical aberration, trefoil aberration and so on). Furthermore, the aberration of the human's eyes is not stationary and dynamically varies with time (D. R. Williams, & Hofer, H. Formation and Acquisition of the Retinal Image. In: J. S. W. Leo M. Chalupa (Ed.), The Visual Neurosciences, the MIT Press, Cambridge, Mass., London, England, 2003). The existing VEP inspection only corrects the low order aberration of human's eyes by ametropia compensation of the lens, and a correction lens with a high degree of separation can't accurately compensate the low order aberration. The existence of the residual low order aberration and the high order aberration of the human's eyes less affect the VEP inspection at a lower spatial frequency. However, when an image with a higher spatial frequency is utilized to stimulate for the VEP inspection, and an abnormal phenomenon is found, it can't be determined wither there is abnormal for the visual pathway and perhaps it is caused by the optical aberration of the testee which is not corrected ("Electrophysiological research on the effects of optical-induced ametropia on transfer of visual signal and response of visual signals in the visual cortex", Master degree thesis of Laiqing Xie, Tianjin Medical University, 2009). Therefore, when the VEP is utilized to evaluate the visual nerve function and to objectively inspect eyesight of human's eyes, the influence of the human's eyes aberration on the projection of the visual stimulation to the retina within the eye ground has to be eliminated so as to obtain an accurate result for the VEP inspection.

SUMMARY

One aspect of the present disclosure provides an adaptive optical objective inspection instrument for optic nerve function comprising: a sub-system for measuring wave aberration of human's eyes, including a near infrared beacon light source, an intermediate optical system, a wavefront corrector and a wavefront sensor, configured to measure and obtain wave aberration of human's eyes of testee, the intermediate optical system being arranged along an optical path between the near infrared beacon light source and the wavefront sensor, and the wavefront corrector being arranged in the optical path of the intermediate optical system; a sub-system for correcting wave aberration of human's eyes, including the intermediate optical system, the wavefront corrector and a control unit, the control unit configured to drive and control the wavefront corrector to correct the wave aberration of human's eyes of the testee according to the measured wave aberration of human's eyes of the testee; and a sub-system for objectively inspecting optic nerve function, including a visual stimulus displaying unit and a system for collecting visual evoked potential signal, wherein the testee observes a visual stimulation displayed on the stimulus displaying unit through the intermediate optical system and the wavefront corrector, and the visual evoked potential signal at a dermal surface of the head is recorded through the system for collecting visual evoked potential signal.

Alternatively, the wavefront corrector is selected from a deformable mirror, a liquid crystal wavefront corrector, a micromachined membrane deformable mirror, micro electromechanical deformable mirror, a bimorph deformable reflective mirror and a liquid deformable mirror.

Alternatively, the wavefront sensor is selected from a Hartmann wavefront sensor based on a micro lens array, a Hartmann wavefront sensor based on a micrograting array, a curvature wavefront sensor or a pyramid wavefront sensor.

Alternatively, the stimulus displaying unit is selected from a CRT display, a commercial projector, a liquid crystal display, a plasma display, electroluminescent display and an organic light-emitting display.

Alternatively, the video processing circuit combines an R channel signal and a B channel signal in a common video output and implements a gray scale of 14 bits or more.

Alternatively, the intermediate optical system comprises a collimator mirror, a first reflective mirror, a first spectroscope, a first light beam matching telescope, a second light beam matching telescope, a second reflective mirror and second spectroscope arranged in turn in a light path between the near infrared beacon light source and the wavefront sensor; and the wavefront corrector is arranged in a light path between the first light beam matching telescope and the second light beam matching telescope.

Alternatively, the wave aberration of human's eyes is calculated based on an actual light spot signal received by the wavefront sensor and a light spot signal generated by incidence of a standard plane wave and functioning as a referencing data.

Alternatively, the subsystem for objectively inspecting optic nerve function further comprises a video processing circuit, the video processing circuit is visually stimulated by flashing or image having a different spatial frequencies and different contrast, and the stimulation is displayed on the visual stimulus displaying unit; and the recorded visual evoked potential signal is contrasted and analyzed to objectively inspect and evaluate the optic nerve function.

As compared with the prior art, the present disclosure firstly apply an adaptive optical correction of human's eyes aberration to VEP inspection. With respect to the existing VEP inspection, the present system measures and corrects low order and high order optical aberrations of human's eyes by the adaptive optical system. In such a situation, the retina is visually stimulated by flashing or image so as to eliminate influence of the low order and high order optical aberrations of human's eyes on the visual evoked potential, thereby eliminate the projection of the visual stimulation onto the retina in an eye ground. Finally, the accuracy of the objective inspection and evaluation on the visual nerve function may be enhanced.

BRIEF DESCRIPTION OF THE DRAWINGS

The above and other objects, features and advantages of the present disclosure would be apparent by illustrating the optional embodiments of the present disclosure in conjunction with the following figures, in which.

DETAILED DESCRIPTION

In order to definitely illustrate implementations of the present disclosure, the alternative embodiments of the present disclosure will be described in detail by referring to FIG. 1. During description, unnecessary details and functions are omitted for confuse the understanding of the present disclosure.

Figure 1:
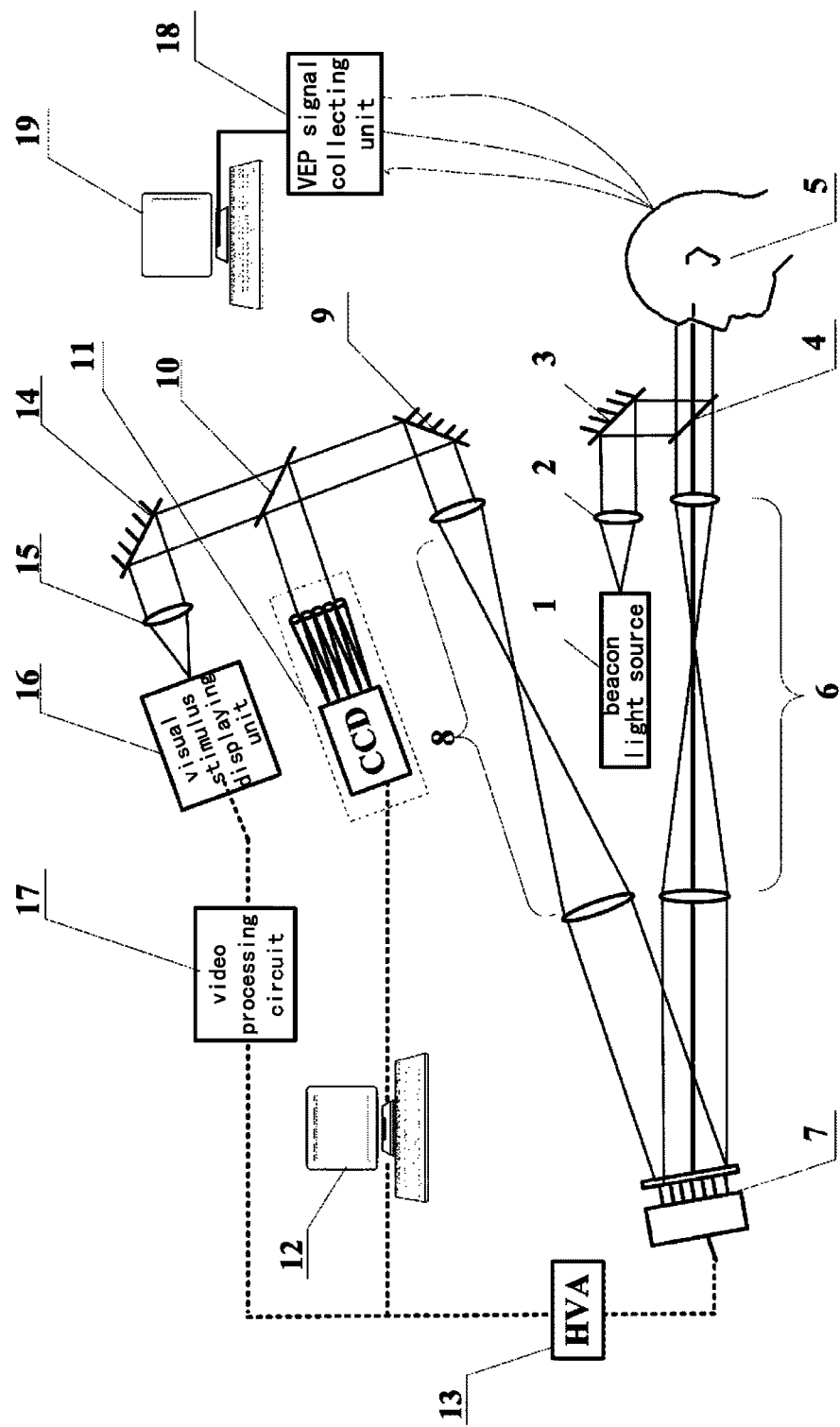
FIG. 1 is a principle block diagram of the configuration of the present disclosure.

FIG. 1 is a principle block diagram of the configuration of the present disclosure.

As shown in FIG. 1, the adaptive optical objective inspection instrument for optic nerve function according to the present disclosure comprises a near infrared beacon light source 1, a collimator mirror 2, a first reflective mirror 3, a first spectroscope 4, a first light beam matching telescope 6, a wavefront corrector 7, a second light beam matching telescope 8, a second reflective mirror 9, a second spectroscope 10, a wavefront sensor 11, a control computer 12, a high voltage amplifier 13, a third reflective mirror 14, an optical imaging system 15, a visual stimulus displaying unit 16, a video processing circuit 17, a VEP signal collecting unit 18 and a data processing computer 19. The testee is indicated by a reference sign of "5".

The adaptive optical objective inspection instrument for optic nerve function according to the present disclosure comprises three sub-systems: a sub-system for measuring wave aberration of human's eyes, a sub-system for correcting wave aberration of human's eyes and a VEP sub-system for collecting and analyzing signals.

In the sub-system for measuring wave aberration of human's eyes, a light emitted from the near infrared beacon light source 1 is collimated by the collimator mirror 2, reflected by the first reflective mirror 3 and the first spectroscope 4 into a pupil of human's eyes 5; the light reflected by the human's eyes 5 passes through the first spectroscope 4 and the first light beam matching telescope 6 and is reflected by the wavefront corrector 7, passes through the second light beam matching telescope 8 and is reflected by the second reflective mirror 9 and the second spectroscope 10 into the wavefront sensor 11; the wavefront sensor 11 delivers the received light spot signal to the control computer 12 to be processed to wave aberration of human's eyes.

Figure 3A:
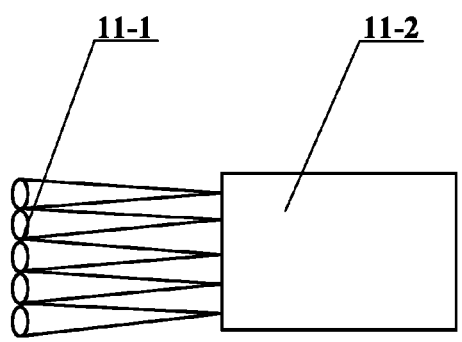
FIG. 3a is a schematic view of the configuration of a Hartmann wavefront sensor based on a micro lens array.

The wavefront corrector 11 may be a Hartmann wavefront sensor based on a micro lens array, a Hartmann wavefront sensor based on a micro grating array, a curvature wavefront sensor or a pyramid wavefront sensor. Herein, the Hartmann wavefront sensor based on micro lens array is taken as an example to illustrate its principle for measuring. As shown in FIG. 3a, the Hartmann wavefront sensor based on micro lens array is constituted of a micro lens array 11-1 and a photo detector (such as a CCD detector) 11-2, in which the photo detector 11-2 is located at a focal plane of the micro lens array 11-1.

The principle of the Hartmann wavefront sensor based on micro lens array is shown as follows: an incidence light passes through the micro lens array 11-1 to form a light spot array on its focal plane so that the whole aperture of the light beam is uniformly divided. A light spot array generated by incidence of the standard plane wave is saved as a referencing data. When a wavefront having a certain aberration is incidence, the inclination of local wavefront on the respective microlens leads to position shift of the light spot on the focal plane of the micro lens array.

The light spot signal received by the photo detector 11-2 may be processed by the computer utilizing a centroid algorithm as follows. The position $(x_i, y_i)$ of the light spot is calculated by the formula ① so as to detect information about the wave plane of the full aperture.:

$$x_i = \frac{\sum_{m=1}^{M}\sum_{n=1}^{N} x_{nm} I_{nm}}{\sum_{m=1}^{M}\sum_{n=1}^{N} I_{nm}}, y_i = \frac{\sum_{m=1}^{M}\sum_{n=1}^{N} y_{nm} I_{nm}}{\sum_{m=1}^{M}\sum_{n=1}^{N} I_{nm}} \qquad ①$$

in which, m=1~M, n=1~N, showing that the sub-aperture is mapped into the corresponding pixel regions on the photo detector 11-2, $I_{nm}$ represents signals received by the $(n,m)^{th}$ pixel on the photo detector 11-2, and $x_{nm}$ and $y_{nm}$ represent x coordinate and y coordinate of the $(n,m)^{th}$ pixel, respectively.

Figure 3B:
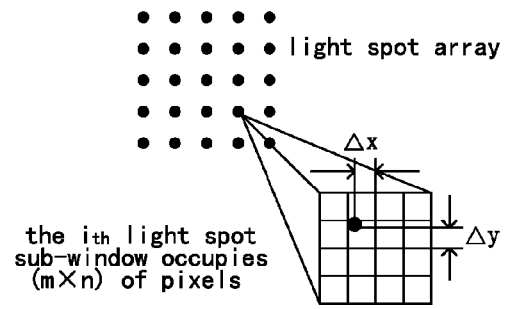
FIG. 3b is a schematic view of a principle of the Hartmann wavefront sensor based on a micro lens array.

Then, a slope $g_{xi}$, $g_{yi}$ of wave aberration of the incidence wavefront is calculated according to the formula ②

$$g_{xi} = \frac{\Delta x}{\lambda f} = \frac{x_i - x_o}{\lambda f}, g_{yi} = \frac{\Delta y}{\lambda f} = \frac{y_i - y_o}{\lambda f} \qquad ②$$

in which, $(x_0, y_0)$ represents a reference position of the center of the light spot obtained by standardizing the Hartmann sensor for an ideal plane wave; when the Hartmann sensor detects wavefront aberration, the center of the light sport shifts to $(x_i, y_i)$, in which $\lambda$ is a wavelength of the incidence light and f is a focal length of the microlens. Thus, the Hartmann wavefront sensor detects signal and the schematic view of its principle is shown in FIG. 3b.

In the sub-system for correcting wave aberration of human's eyes, the control computer 12 utilizes a direct slop method to obtain a control voltage for the wavefront corrector 7 according to a slope data of wave aberration of human's eyes. Such a control voltage is amplified by the high voltage amplifier 13 to drive the wavefront corrector 7 to generate a corresponding change so as to correct the wave aberration of human's eyes.

After the correction of the wave aberration of human's eyes is completed, the VEP signal may be collected and analyzed. A VEP measuring software installed in the computer 12 generates visual stimulation by a flash or an image having different spatial frequencies and different contrasts, to be processed by the video processing circuit 17 and then displayed on the visual stimulus displaying unit 16. The testee observes the visual stimulation presented on the visual stimulus displaying unit 16 through the first spectroscope 4, the light beam matching telescope 6, the wavefront corrector 7, the light beam matching telescope 8, the second reflective mirror 9, the second spectroscope 10, the third reflective mirror 14 and the imaging lens 15; the visual evoked potential signal at the dermal surface of the head is recorded through the VEP signal collection unit 18 and input to the data processing computer 19. Thus, by comparing and analyzing the recorded visual evoked potential signal, the optic nerve function may be objectively inspect and evaluated.

The wavefront corrector 7 may be selected from a deformable reflective mirror, a liquid crystal wavefront corrector, a micromachined membrane deformable mirror, a micro electromechanical deformable mirror, a bimorph deformable mirror, a liquid deformable mirror.

The wavefront sensor 11 may be selected from a Hartmann wavefront sensor based on a micro lens array, a Hartmann wavefront sensor based on a micro grating array (cf. Chinese invention patent ZL03126431.X), a curvature wavefront sensor or a pyramid wavefront sensor.

The visual stimulus displaying unit 16 may be selected from a CRT display, a commercial projector, a color liquid crystal display, a plasma display, electroluminescent display and an organic light-emitting display.

The video processing circuit 17 may combine an R channel signal and a B channel signal in a common video output and implements a gray scale of 14 bits (16384 steps) or more so as to meet the requirement of fine adjustment of contrast for the visual stimulation. For example, the video processing circuit 17 may utilizes a particular circuit disclosed by a Chinese Utility Patent ZL02220968.9.

Figure 2:
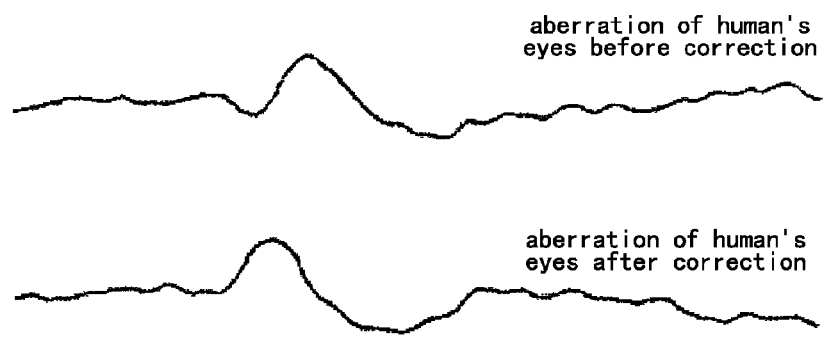
FIG. 2 is a schematic view of the influence of the human's eyes optical aberrations on a visual evoked potential signal of an image.

FIG. 2 is a schematic view of the influence of the human's eyes optical aberrations on a visual evoked potential signal of an image. The influence of human's eyes aberration on the VEP signal is indirectly validated by Laiqing Xie, Tianjin Medical University, superposing spherical lens with astigmatism. The present disclosure eliminates influence of the low order and high order optical aberrations of human's eyes on the visual evoked potential, thereby eliminate the projection of the visual stimulation onto the retina in an eye ground, by the adaptive optical system measuring and correcting the human's eyes aberration, so as to enhance the accuracy of the objective inspection and evaluation on the visual nerve function.

According to embodiments of the present disclosure, the adaptive optical system measures and corrects aberrations of human's eyes. In such a situation, the retina is visually stimulated by flashing or image so as to eliminate influence of the low order and high order optical aberrations of human's eyes on the visual evoked potential, thereby eliminate the projection of the visual stimulation onto the retina in an eye ground. Finally, the accuracy of the objective inspection and evaluation on the visual nerve function may be enhanced.

The present invention has been illustrated in conjunction with the alternative embodiments. It should be understood for those skilled in the art that there are various alternation, substitution and addition without deviating from the spirit and scope of the present invention. Thus, the scope of the present invention is not limited to the specific embodiments as mentioned above, but is defined by the accompany claims.

What is claimed is:

1. An adaptive optical objective inspection instrument for optic nerve function comprising:
   a sub-system for measuring wave aberration of human's eyes, including a near infrared beacon light source, an intermediate optical system, a wavefront corrector and a wavefront sensor, configured to measure and obtain wave aberration of human's eyes of testee, the intermediate optical system being arranged along an optical path between the near infrared beacon light source and the wavefront sensor, and the wavefront corrector being arranged in the optical path of the intermediate optical system;
   a sub-system for correcting wave aberration of human's eyes, including the intermediate optical system, the wavefront corrector and a control unit, the control unit configured to drive and control the wavefront corrector to correct the wave aberration of human's eyes of the testee according to the measured wave aberration of human's eyes of the testee; and
   a sub-system for objectively inspecting optic nerve function, including a visual stimulus displaying unit and a system for collecting visual evoked potential signal, wherein the testee observes a visual stimulation displayed on the visual stimulus displaying unit through the intermediate optical system and the wavefront corrector, and the visual evoked potential signal at a dermal surface of the head is recorded through the system for collecting visual evoked potential signal.

2. The adaptive optical objective inspection instrument for optic nerve function according to claim 1, wherein an objective inspection and estimation for the visual nerve are selected from the visual evoked potential by flashing or image.

3. The adaptive optical objective inspection instrument for optic nerve function according to claim 1, wherein the wavefront corrector is selected from the group consisting of a deformable mirror, a liquid crystal wavefront corrector, a micromachined membrane deformable mirror, micro electromechanical deformable mirror, a bimorph deformable reflective mirror and a liquid deformable mirror.

4. The adaptive optical objective inspection instrument for optic nerve function according to claim 1, wherein the wavefront sensor is a Hartmann wavefront sensor based on a micro lens array, a Hartmann wavefront sensor based on a micro grating array, a curvature wavefront sensor or a pyramid wavefront sensor.

5. The adaptive optical objective inspection instrument for optic nerve function according to claim 1, wherein the visual stimulus displaying unit is selected from the group consisting of a CRT display, a commercial projector, a liquid crystal display, a plasma display, electroluminescent display and an organic light-emitting display.

6. The adaptive optical objective inspection instrument for optic nerve function according to claim 1, wherein the video processing circuit combines an R channel signal and a B channel signal in a common video output and implements a gray scale of 14 bits or more.

7. The adaptive optical objective inspection instrument for optic nerve function according to claim 1, wherein the intermediate optical system comprises a collimator mirror, a first reflective mirror, a first spectroscope, a first light beam matching telescope, a second light beam matching telescope, a second reflective mirror and second spectroscope arranged in turn in a light path between the near infrared beacon light source and the wavefront sensor; and the wavefront corrector is arranged in a light path between the first light beam matching telescope and the second light beam matching telescope.

8. The adaptive optical objective inspection instrument for optic nerve function according to claim 1, wherein the wave aberration of human's eyes is calculated based on an actual light spot signal received by the wavefront sensor and a light spot signal generated by incidence of a standard plane wave and functioning as a referencing data.

9. The adaptive optical objective inspection instrument for optic nerve function according to claim 1, wherein the subsystem for objectively inspecting optic nerve function further comprises a video processing circuit,
the video processing circuit is visually stimulated by flashing or image having a different spatial frequencies and different contrast, and the stimulation is displayed on the visual stimulus displaying unit; and
comparing and analyzing the recorded visual evoked potential signal to objectively inspect and evaluate the optic nerve function.

* * * * *